United States Patent [19]

Pepe et al.

[11] Patent Number: 4,668,716

[45] Date of Patent: May 26, 1987

[54] NOVEL FATTY ETHENOID ACYLAMINOORGANOSILICON COMPOUNDS AND THEIR USE AS A COUPLING AGENT

[75] Inventors: Enrico J. Pepe, Amawalk, N.Y.; James G. Marsden, Rowayton, Conn.

[73] Assignee: Union Carbide Corporation, Danbury, Conn.

[21] Appl. No.: 804,892

[22] Filed: Dec. 5, 1985

Related U.S. Application Data

[62] Division of Ser. No. 537,671, Sep. 30, 1983, Pat. No. 4,584,138.

[51] Int. Cl.$^4$ .............................................. C08K 9/06
[52] U.S. Cl. .................................... 523/213; 523/214; 524/601
[58] Field of Search ................. 523/213, 214; 524/601

[56] References Cited

U.S. PATENT DOCUMENTS

| | | | |
|---|---|---|---|
| 2,928,858 | 3/1960 | Morehouse | 260/448.8 |
| 2,929,829 | 3/1960 | Morehouse | 260/448.2 |
| 3,249,461 | 5/1966 | TeGrotenhuis | 117/76 |
| 3,537,882 | 11/1970 | Wiggill | 117/72 |
| 3,681,266 | 8/1972 | Domba | 260/25 |
| 3,720,699 | 3/1973 | Stoddard | 260/448.8 |
| 3,746,738 | 7/1973 | Pepe et al. | 260/46.5 |
| 3,755,354 | 8/1973 | Holub et al. | 260/326 |
| 3,787,439 | 1/1974 | Holub et al. | 260/326 |
| 3,813,425 | 5/1974 | Traver | 260/448.2 |
| 3,956,353 | 5/1976 | Plueddemann | 260/448.8 |
| 3,959,327 | 5/1976 | Pepe et al. | 260/448.8 |
| 4,209,455 | 6/1980 | Pepe | 260/448.8 |
| 4,284,548 | 9/1981 | Kaufman et al. | 260/38 |
| 4,312,993 | 1/1982 | Martin | 556/419 |
| 4,584,138 | 4/1986 | Pepe et al. | 260/404.5 |

OTHER PUBLICATIONS

CA 84:59633W (1975), Reaction of 3-Aminopropyl Triethoxysilane with Carboxylic Acid Chlorides (1975).

*Primary Examiner*—Melvyn I. Marquis
*Attorney, Agent, or Firm*—Paul W. Leuzzi

[57] ABSTRACT

A novel class of fatty ethenoid acylaminorganosilicon compounds are provided which are useful as coupling agents for fiber glass reinforced resin composites.

1 Claim, No Drawings

NOVEL FATTY ETHENOID ACYLAMINOORGANOSILICON COMPOUNDS AND THEIR USE AS A COUPLING AGENT

This application is a division of prior U.S. application Ser. No. 537,671 filing date 9/30/83, now U.S. Pat. No. 4,584,138.

BACKGROUND OF THE INVENTION

1. Field of the Invention

The instant invention relates to a novel class of acylaminoorganosilicon compounds and their use as coupling agents. More specifically, the novel class of acylaminoorganosilicon compounds are those containing a fatty ethenoid substituent.

2. Prior Art

Acylaminoorganosilicon compounds have been generally known since the pioneering work performed by Morehouse as reported in U.S. Pat. Nos. 2,929,829 and 2,928,858. The novel acylaminoorganosilicon compounds taught in these references were considered useful as, among other things, acid-base indicators; additives for silicon products, such as oils and gums; thermosetting resins for coating materials; and ultraviolet ray absorbers.

Subsequent to the work performed by Morehouse, improvements based on new and useful acylaminoorganosilicon compounds were discovered. In U.S. Pat. No. 3,249,461, the use of a conjugated olefin containing acylaminoorganosilicon compounds were taught as effective fiber glass reinforcing agents. In U.S. Pat. No. 3,681,266, a distinct class of acylaminoorganosilicon compounds was fluorine modified to provide a coating material that is useful as a water repellant. In U.S. Pat. No. 3,720,699, a new and useful class of haloorganoacylaminoorganosilicon compounds are reported to be useful as a coating material.

A variance on the theme, U.S. Pat. No. 3,755,354 is directed to amide acid and imido-substituted organosilicon compounds that are reportedly useful as glass fiber coupling agents. In a closely related U.S. Pat. No. 3,787,439, imido-substituted organopolysiloxanes were disclosed, including conjugated, unsaturated acylaminoorganosilicon compounds, as additives for glass fibers.

In U.S. Pat. No. 3,959,327, acylaminoorganosilicon compounds with thio-containing substituents were reported as plasticizers and coupling agents.

A new class of complex acylaminoorganosilicon compounds was reported in U.S. Pat. Nos. 4,209,455 and 4,284,548. In each the mono- and bis-silanes were characterized by a single acylamino group and at least one secondary or tertiary aminoorgano group. These novel compositions were considered useful in fiber sizes.

In U.S. Pat. No. 3,746,738, acylaminoorganosilicon compounds that contained various pendant silanes were described as useful glass fiber sizes.

In U.S. Pat. No. 3,537,832, silylated polymers were prepared by amidation of acid chloride modified polymers with aminoorganosilanes for use as coating materials.

Finally, CA 84:59633W teaches a stearoyl and oleoyl acylaminoorganosilicon compounds.

Although the art is replete with improvements in and modifications of acylaminoorganosilicon compounds, it is believed that the instant fatty ethenoid acylaminoorganosilicon compounds containing bis-silane and/or multiple unsaturation in the fatty constituents are novel and that their use as coupling agents is also novel.

OBJECTIVES OF THE INVENTION

It is an object of this invention to provide a novel class of acylaminoorganosilicon compounds.

It is a further object of this invention that the novel class of acylaminoorganosilicon compounds provided are useful as coupling agents, preferably for fiber glass reinforced resin composites.

As a coupling agent, it is an object of this invention that the novel class of acylaminoorganosilicon compounds yield improved composite properties as well as improved glass fiber and roving properties.

It is a further object of this invention that as a coupling agent the novel class of acylaminoorganosilicon compounds provide roving abrasion resistance at least comparable to existing coupling agents.

It is another object of this invention that as a coupling agent, the novel class of acylaminoorganosilicon compounds provide a vehicle for controlling fiber stiffness.

Other objects of this invention will become apparent from the detailed disclosure and examples set forth herein.

SUMMARY OF THE INVENTION

In accordance with the present invention there is provided a novel class of acylaminoorganosilicon compounds. This novel class of acylaminoorganosilicon compounds contain a fatty ethenoid substituent and is represented by the general formula:

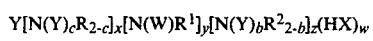

$$Y[N(Y)_cR_{2-c}]_x[N(W)R^1]_y[N(Y)_bR^2_{2-b}]_z(HX)_w$$

wherein R and $R^1$ are individually selected from the group consisting of divalent alkylene groups containing from two to six carbon atoms inclusive, divalent arylene groups containing from six to twelve carbon atoms inclusive, divalent alkyl substituted arylene groups containing from seven to twenty carbon atoms inclusive, and a divalent group of the formula

$$-\overset{O}{\underset{\|}{C}}R^3-$$

wherein $R^3$ is a divalent alkylene group containing from two to six carbon atoms inclusive; $R^2$ is a monovalent alkyl or aryl group containing from one to ten carbon atoms or hydrogen; W is either hydrogen, or

$$-\overset{O}{\underset{\|}{C}}R^4$$

wherein $R^4$ is a monovalent hydrocarbon group containing from 8 to 24 carbon atoms and containing at least one double bond; Y is selected from the group consisting of hydrogen;

$$-\overset{O}{\underset{\|}{C}}R^4$$

wherein $R^4$ is as defined above; $R^2$; and $-R^5Si(OR^6)_{3-a}(R^7)_a$ wherein $R^5$ is a divalent alkylene group containing from two to six carbon atoms inclusive, $R^6$ and $R^7$ are individually a monovalent alkyl or aryl group containing from one to six carbon atoms inclusive; and $R^6$ may also be a silicon containing moiety wherein the oxygen atom is directed bonded to the silicon atom of the $R^6$ silicon containing moiety; and a has a value of zero, one, or two; b has a value of zero, one or two; c has a value of zero or one; x and y have values such that x+y equal one to thirty with the proviso that x is at least one; z is zero or one; X is as hereinafter defined; w has a value equal to from zero to the sum of x+y+z provided that w does not exceed the total nitrogen atom in free amine form; with the proviso that at least one Y is $-R^5Si(OR^6)_{3-a}(R^7)_a$; and at least one other Y is

$$\underset{CR^4;}{\overset{O}{\parallel}}$$

and when only one Y is $-R^5Si(OR^6)_{3-a}(R^7)_a$ then $R^4$ contains at least two double bonds; and when x=1, y=0 and z=0 then c=1.

As previously set forth, this novel class of acylaminoorganosilicon compounds is useful as coupling agents. It should be mentioned in this regard that the proviso that when only one Y is $-R^5Si(OR^6)_{3-a}(R^7)_a$ then $R^4$ must contain at least two double bonds is only relevant to the novelty of the compound. It is believed that $R^4$ can contain only one double bond and still have an acylaminoorganosilicon compound that will be useful as a coupling agent.

DETAILED DESCRIPTION OF THE INVENTION

The novel class of fatty ethenoid acylaminoorganosilicon compounds represented by formula I above can be prepared by a variety of known techniques. The basic reaction is the acylation of an aminoorganosilane by reaction with a carboxylic organic acid, a carboxylic organic acid halide, an ester or anhydride derivative of a carboxylic organic acid. The aminoorganosilanes suitable for acylation in the instant invention are represented by the formula:

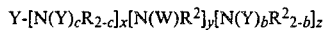
$$Y-[N(Y)_cR_{2-c}]_x[N(W)R^2]_y[N(Y)_bR^2_{2-b}]_z$$

wherein Y is as defined above but excluding

$$\underset{-CR^4}{\overset{O}{\parallel}}$$

and X, R, $R^1$, $R^2$, b, c, x, y and z are as defined above. At least one Y must be $-R^5Si(OR^6)_{3-a}(R^7)_a$ and at least one other Y must be hydrogen.

Preferably, the aminoorganosilanes are such that R and $R^1$ are ethylene or propylene, $R^2$ is methyl or hydrogen, $R^5$ is propylene, $R^6$ and $R^7$ are methyl or ethyl, a=0 or 1, b=0 or 1, c=1, x=1 to 4, y=0 to 3 and z=0 or 1. Illustrative of such primary and secondary aminoorganosilanes are gamma-aminopropyltriethoxysilane, gamma-aminopropylmethyldiethoxysilane, gamma-aminopropylethyldiethoxysilane, gamma-aminopropylphenyldiethoxysilane, delta-aminobutyltriethoxysilane, delta-aminobutylmethyldiethoxysilane, delta-aminobutylethyldiethoxysilane, delta-aminobutylphenyldiethoxysilane, N-methyl-gamma-aminopropyltriethoxysilane, N-phenyl-gamma-aminopropyltriethoxysilane, N-butyl-gamma-aminopropylmethyldiethoxysilane and the like.

Suitable acylation reagents are those represented by the general formula

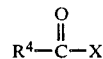
$$R^4-\overset{O}{\underset{\parallel}{C}}-X$$

where $R^4$ is a monovalent hydrocarbon group containing anywhere from 8 to 24 carbon atoms and at least one double bond and X is a halogen atom, a hydroxyl group, an ester group ($-OR^8$) or an anhydride group ($-OOCR^9$). Wherein $R^8$ and $R^9$ are individually monovalent hydrocarbon groups. Although such a composition may be synthetically prepared from petroleum based materials and as such used in the present invention, it is preferred to employ those materials derived from a fatty acid (hence the term "fatty" will be employed herein; however it should not be construed to mean the acids are derived solely from non-petroleum based materials). Fatty acids are principally derived from the body fat of animals, such as lard and tallow; from fruit pulp, such as palm and olive; the seed of plants, such as cottonseed, peanut, corn, safflower, sesame, sunflower, rapeseed, mustardseed, soybean, and linseed; and the like.

Common monoethenoid fatty acids include abtusilic, capraleic, 10-undecylenic, lauroleic, physeteric, myristoleic, palmitoleic, petroselinic, petroselaidic, oleic, elaidic, vaccenic, gadoleic, cetaleic, erucic, brassidic, selacholeic, ximenic and lumequoic to name but a few.

The polyethenoid fatty acids include, but are not limited to, sorbic, linoleic, linolelaidic, hiragonic, eleostearic, punicic, linolenic, elaidolinolenic, psuedoeleostearic, moroctic, parinaric, arachidonic, clupanodonic, nisinic and the like.

The fatty acids useful in the present invention are considered to include both those containing conjugated as well as nonconjugated double bonds.

Preferably, the fatty acid contains eight to eighteen carbon atoms; more preferably the fatty acid is one derived from linseed. Such fatty acids are commercially available, such as from Procter & Gamble, and contain an assortment of fractions. Illustrative of the fractional content of a commercial grade linseed acid is the data in Table I below.

TABLE I

| FRACTION | PERCENT (WEIGHT) |
|---|---|
| $C_{14}$, $C_{12}$, $C_{10}$, $C_8$, and lowers | 1.6 + 0.1% |
| $C_{16}$ palmitic | 5.5 ± 0.3% |
| $C_{18}$ stearic | 3.6 ± 0.2% |
| $C_{18}$ oleic 1×(=) | 17.9 ± 0.9% |
| $C_{18}$ linoleic 2×(=) | 18.0 ± 0.9% |
| $C_{18}$ linolenic 3×(=) | 50.7 ± 2.5% |
| higher than $C_{18}$ | 2.7 ± 0.2% |

The free fatty acid is converted to the acylation reagents by well known techniques. For instance, when X is to be halogen, the fatty acid is converted at room temperature or higher by simple addition of thionyl halide to the fatty acid and thereafter removal of sulfur dioxide and hydrogen chloride is effected. If an fatty acid ester is desired, it is obtained by catalyzed esterification with alcohols and fatty acid and removal of by-product water. If the anhydride derivative is desired the anhydride derivative is produced by catalyzed dehydration of the fatty acid. Most, if not all, of these acylation reagents are commercially available.

The details as to the acylation reaction conditions between the monoprimary and or secondary aminosilane and the carboxylic organic acid or derivative are more fully set forth in U.S. Pat. No. 2,929,829 issued Mar. 22, 1960.

Where mono aminoorganosilicon compounds are reacted with carboxylic organic acid halides, a tertiary alkyl amine, such as Et₃N or pyridine may be employed to remove the HM and aid the completion of the acylaminoorganosilicon compound. In other instances an excess of aminoorganosilicon compound instead of the tertiary alkyl amine or pyridine is used to produce a mixture of aminoorganosilicon hydrogenhalide and the corresponding fatty ethenoid acylaminoorgano silicon compound. In this latter approach the aminoorganosilicon hydrogenhalide compounds remain as a water compatible co-reactive silane component which in some instances may provide a substantial benefit to end use handling and performance of the coupling agent.

An illustrative reaction between acylation reagents and aminoorganosilanes with primary and secondary amino groups is depicted below:

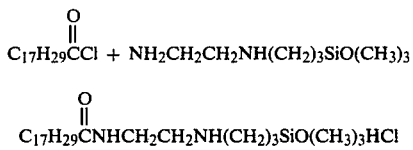

$$C_{17}H_{29}CCl + NH_2CH_2CH_2NH(CH_2)_3SiO(CH_3)_3$$

$$C_{17}H_{29}CNHCH_2CH_2NH(CH_2)_3SiO(CH_3)_3 HCl$$

For many coupling agent applications it is preferred to use carboxylic acid chloride acylating reagents because they are readily available, highly reactive and least complicated by undesirable side reactions. Optional removal of HCl is sometimes advantageous.

Aminoorganosilanes having two or more amino groups and one or more silane groups are reacted with carboxylic organic acid halide to obtain a fatty ethenoid acylaminoorganosilicon compound which can have a combination of fatty acylamino, free amino and amine hydrogen halide groups as well as two or more silane groups.

Suitable aminoorganosilanes containing two or more amino groups include, but are not limited to, N-beta-(aminoethyl)gamma-aminopropyltrimethoxysilane; N-beta-(aminoethyl)-N-beta-(aminoethyl)gamma-aminopropyltrimethoxysilane; (CH₃O)₃SiCH₂Ch₂CH₂NHCH₂CH₂NH₂, (C₂H₅O)₂(CH₃)SiCH₂CH₂CH₂(NHCH₂CH₂)₃NHCH₂CH₂CH₂Si(CH₃)(OC₂H₅)₂, (CH₃O)₃SiCH₂CH₂CH₂NHCH₂C₆H₄CH₂NHCH₂CH₂CH₂Si(OCH₃)₃, and (CH₃O)₂(CH₃)SiCH₂CH₂CH₂NHCH₂CH₂NHCH₂CH₂CH₂Si(CH₃)(OCH₃)₂.

Once again, reference is made to U.S. Pat. No. 2,929,829 for particulars relative to reaction conditions.

For production of water dilutable coupling agents from polyaminoorgano(poly)silanes, it is preferred to add carboxylic acid chloride slowly to a well stirred solution of silane in methanol, ethanol or the like at from 0° to 150° C. preferably 25°-70° C. The in situ formation of aminoorgano hydrogen halide salt groups which occurs during this reaction provides the product with water solubility or dispersibility. This preferred process for fatty acylated derivatives of polyaminoorgano(poly)silane compounds generally is used to produce the same molar concentration of acylated amine and amine hydrogen halide salt groups. The molar concentration of free amino groups will largely depend on the extent of acylation initially undertaken in this process and can vary widely.

The novel compounds of this invention are complex structures, but can be produced by alternate methods. In one such method a polyalkyleneamine is reacted with the carboxylic organic acid, its acid halide or anhydride to provide a partial acylamino derivative, which is also an amino containing intermediate that is subsequently silylated by conventional means to provide the acylaminoorganosilicon compound desired.

This latter silylation reaction between partially acylated polyaltyleneamine and organo functional silane is preferably an amine arkylation reaction with a chloroorganosilane ester and generally requires higher reaction temperatures. Usually, it is necessary to premix reactants and heat to between 60° C. and 140° C. Preferably a reaction temperature between 80° and 120° C. is desirable. The reaction can be effected over any reasonable time period to produce some reaction product but usually it is desirable to follow the course of the reaction by titration of chloride ion. A non aqueous potentiometric titration of generated chloride ion with standardized silver nitrate serves nicely.

This process has a tendency to produce higher viscosity products with varying amounts of polysiloxane product in place of the full amount of silane ester groups. Subsequent dilute aqueous dispersions also show a somewhat greater tendancy to destabilize with time.

In general, we prefer to silylate polyalkyleneamines according to the teachings of U.S. Pat. No. 3,746,738 and to subsequently acylate as previously described.

In all of the reactions set forth above the desired end product is a fatty ethenoid acylaminoorganosilicon compound selected from the class represented by the general formula:

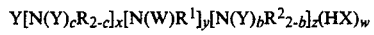

$$Y[N(Y)_cR_{2-c}]_x[N(W)R^1]_y[N(Y)_bR^2_{2-b}]_z(HX)_w$$

Preferably, the fatty ethenoid acyl aminoorganosilicon compounds are such that R and R¹ are alkylene radicals and more preferably ethylene or propylene, R² is methyl or hydrogen, R⁴ is a monovalent hydrocarbon radical containing 1 to 20 carbon atoms and at least two double bonds R⁵ is propylene, R⁶ and R⁷ are methyl or ethyl, a=0 or 1, b=0 or 1, c=1, x=1 to 4, y=0 to 3 and z=0 or 1, and at least one Y is —R⁵Si(OR⁶)₃₋ₐ(R⁷)ₐ and at least one other Y is

$$-CR^4.$$
$$\overset{O}{\underset{\|}{}}$$

Exemplary of the fatty ethenoid acylaminoorganosilicon compounds are set forth in Table I below:

TABLE I

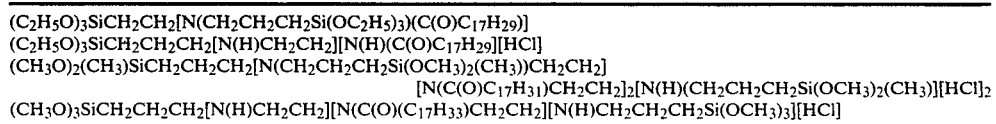

(C₂H₅O)₃SiCH₂CH₂[N(CH₂CH₂CH₂Si(OC₂H₅)₃)(C(O)C₁₇H₂₉)]
(C₂H₅O)₃SiCH₂CH₂CH₂[N(H)CH₂CH₂][N(H)(C(O)C₁₇H₂₉)][HCl]
(CH₃O)₂(CH₃)SiCH₂CH₂CH₂[N(CH₂CH₂CH₂Si(OCH₃)₂(CH₃))CH₂CH₂]
[N(C(O)C₁₇H₃₁)CH₂CH₂]₂[N(H)(CH₂CH₂CH₂Si(OCH₃)₂(CH₃))][HCl]₂
(CH₃O)₃SiCH₂CH₂CH₂[N(H)CH₂CH₂][N(C(O)(C₁₇H₃₃)CH₂CH₂][N(H)CH₂CH₂CH₂Si(OCH₃)₃][HCl]

TABLE I-continued (CH₃O)₃SiCH₂CH(CH₃)[N(H)CH₂C₆H₄CH₂][N(C(O)C₁₇H₃₁)CH₂C₆H₄CH₂][N(H)—CH(CH₃)CH₂Si(OCH₃)₃][HCl]₂
(CH₃O)₂(CH₃)SiCH₂CH₂CH₂[N(C(O)C₁₇H₂₉)CH₂CH₂][N(C(O)C₁₇H₂₉)CH₂CH₂CH₂CH₂Si(CH₃)(OCH₃)₂
(C₂H₅O)₃SiCH₂CH₂CH₂N(H)C(O)C₁₇H₂₉
(CH₃O)₃SiCH₂CH₂CH₂NHCH₂CH₂N(H)C(O)C₁₇H₂₉(HCl)
(CH₃O)₃SiCH₂CH₂CH₂N(C(O)C₁₇H₂₉)CH₂CH₂N(H)C(O)C₁₇H₂₉
(CH₃O)₃SiCH₂CH₂CH₂N(C(O)C₁₇H₂₉)CH₂CH₂N(H)CH₂CH₂NH₂(HCl)
(CH₃O)₃SiCH₂CH₂CH₂NHCH₂CH₂N(C(O)C₁₇H₂₉)CH₂CH₂CH₂Si(OCH₃)(HCl)
(CH₃O)₃SiCH₂CH₂CH₂N(C(O)C₁₇H₂₉)CH₂CH₂N(C(O)C₁₇H₂₉)CH₂CH₂CH₂Si(OCH₃)₃
(CH₃O)₃SiCH₂CH₂CH₂[N(H)CH₂CH₂][N(C(O)C₁₇H₂₉)CH₂CH₂CH₂Si(OCH₃)₃][HCl]
(CH₃O)₃SiCH₂CH₂CH₂[N(CH₂CH₂CH₂Si(OCH₃)₃)₃)(C(O)C₁₇H₂₉)]

The fatty ethenoid acylaminoorganosilicon compounds of the present invention find utility in their use as coupling agents.

The use of organofunctional silanes as coupling agents in glass fiber-reinforced composites is a well known and established application. The glass fiber surface is a responsive substrate for reaction with silicon functionality of the coupling agent molecule and the range of organofunctionality of the silanes provides materials that are reactive with most commercial matrix resins. Chemical coupling of the resin to the glass fiber via the silane coupling agent produces stronger composites because of more efficient transfer of stress to the high-strength glass fiber. The chemical nature of the coupling of resin to glass fiber resists degradation of the interface by water, resulting in composites with improved wet mechanical properties and stabilized electrical properties.

While the chemical and physical properties of glass fibers used in reinforcement are very similar, the form of the reinforcement does vary. One efficient form of reinforcement is glass cloth. As the glass fiber is drawn, it is coated with a starch-oil size and then woven into cloth. After weaving, the size is removed via a heat cleaning process, and the glass cloth is "finished" (treated) with a silane coupling agent. The finished cloth is used to prepare laminates by processes such as wet lay-up or compression molding. While glass cloth is an efficient reinforcement, it represents only a fraction of the total glass fiber reinforcement used. The primary limitations of this form of glass fiber are the cost per pound of fiber and limitations in the shape of the composite and fabrication techniques that can be utilized.

The majority of glass fibers used as reinforcement are produced by a similar but slightly different technology. The fibers are drawn in a similar manner but sized (treated) with a mixture of materials, including a silane coupling agent that remains on the fiber through its end use. The form of the reinforcements include continuous roving, woven roving, chopped strand, chopped strand mat, continuous strand mat, etc. Composition of the size will be influenced by the form of the reinforcement, the composite fabrication technique to be used, and the chemistry of the matrix resin. Functionally, the size contains (1) silane coupling agent, (2) film-forming resin, (3) lubricant, and (4) antistatic agent. The specific fatty ethenoid acylaminoorganosilicon is slected on the basis of its reactivity with the matrix resin; however, compatibility with other components in the size must also be considered.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified. For the purposes of these examples Me denotes a methyl group.

EXAMPLES

Example 1

"Fatty" Ethenoid Acylaminoorgano Bis-silane

Into a 1 liter, 3-necked flask equipped with dropping funnel, thermometer, thermosensor, mechanical stirrer, heating mantle, 1 foot ¾" O.D. Vigreaux column, distillation head and receiver was charged 85.3 gms., 0.25 moles of [(MeO)₃SiCH₂CH₂CH₂]₂NH, 35.4 gms., 0.35 moles of triethylamine and 194.2 gms. of toluene. Starting at room temperature, through the dropping funnel was added to the stirred mixture 74.2 gms., 0.25 moles of linseed acid chloride. An exotherm resulted throughout the addition and the reaction mixture temperature was held between 30° and 50° C., by external application of a water/ice bath. After an additional hour of stirring at ~35° C. the total reaction mixture was pressure filtered through a 1 micron filter pad and the resulting Et₃N.HCl salt cake washed with three 50 ml portions of toluene. The combined filtrate and toluene extract of the salt cake was vacuum stripped to 100° C./1 mm Hg pressure to remove toluene, excess triethylamine and any other low boiling components. ¹³C, ²⁹Si NMR and elemental analyses indicate the product structure is

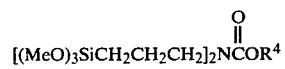

(R⁴=a linseed acid chloride derivative).

Example 2

"Fatty" Ethenoid Acylaminoorgano Bis-Silane/Aminoorgano Bis-Silane Hydrochloride [50 Mole % Mixture]

In much the same equipment setup as described in Example 1, 85.3 gms., 0.25 moles of [(MeO)₃Si(CH₂)₃]₂NH was stirred at 50° C. while 37.11 gms., 0.125 moles of linseed acid chloride was slowly added through a dropping funnel. An exotherm resulted throughout the addition and external cooling was used to control the reaction temperature between 50° and 60° C. The reaction mixture analyzed for 0.98 meq/gm chloride ion [96% of theoretical]. ¹³C, ²⁹Si, NMR and elemental analyses indicate an equimolar mixture of

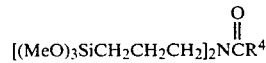

(R=a linseed acid chloride derivative) and [(MeO)$_3$SiCH$_2$CH$_2$CH$_2$]$_2$NH.HCl.

Example 3

"Fatty" Ethenoid Acylamino 25 Mole % Derivative of Diaminoorgano Bis-Silane

In the same equipment setup described in Example 1, 76.8 gms., 0.2 moles of [(MeO)$_3$SiCH$_2$CH$_2$CH$_2$NHCH$_2$]$_2$ dissolved in 106.7 gms., 3.33 moles of methanol was charged. The homogeneous mixture was stirred at room temperature and 29.7 gms., 0.10 moles of linseed acid chloride was slowly added. An exotherm resulted throughout the addition and air cooling was used to control the reaction temperature between 50° and 60° C. The reaction mixture was heated to reflux methanol for one hour, cooled and analyzed for chloride ion [98.3% of theoretical]. The product mixture at 50 wt. % active in methanol, had a calculated average composition:

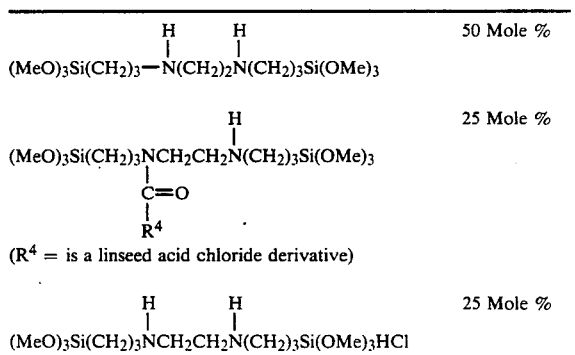

Example 4

"Fatty" Ethenoid Acylaminoorganoamino Bis-Silane Hydrochloride

In much the same manner as described in Example 3, 76.8 gms., 0.2 moles of [(MeO)$_3$SiCH$_2$CH$_2$CH$_2$NHCH$_2$]$_2$ dissolved in 136.4 gms., 4.26 moles of methanol was reacted with 59.4 gms., 0.20 moles of linseed acid chloride. The resulting product, at 50 wt. % active in methanol, has a calculated average composition:

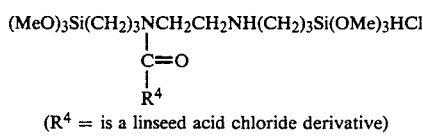

Example 5

Di("Fatty" Ethenoid Acylamino)organo-Bis-Silane

In much the same manner as described in Example 1, 76.8 gms., 0.2 moles of [(MeO)$_3$SiCH$_2$CH$_2$CH$_2$NHCH$_2$]$_2$, 50.6 gms., 0.5 moles of triethyamine and 250 gms. of toluene was reacted with 118.7 gms., 0.4 moles of linseed acid chloride the corresponding di("fatty" ethenoid acylamino)organo-bis-silane

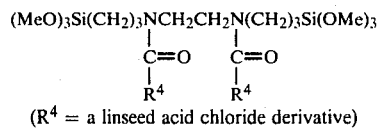

(R$^4$ = a linseed acid chloride derivative)

Example 6

"Fatty" Ethenoid Acylamino Hydrochloride Derivative of Triaminoorganosilane

In much the same manner described for Example 3, 265.4 gms., 1.0 mole of NH$_2$CH$_2$CH$_2$NHCH$_2$CH$_2$NH(CH$_2$)$_3$Si(OMe)$_3$ dissolved in 562.4 gms. of methanol was reacted with 297 gms., 1.0 moles of linseed acid chloride to produce the corresponding "fatty" ethenoid acylamino hydrochloride derivative with the average composition:

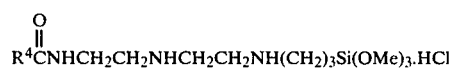

where R$^4$ is a linseed acid chloride derivative

Example 7

"Fatty" Ethenoid Acylamino Hydrochloride Derivative of Diaminoorganosilane

In much the same manner described in Example 3, 222.1 gms., 1.0 moles of NH$_2$CH$_2$CH$_2$NH(CH$_2$)$_3$Si(OMe)$_3$, dissolved in 519.1 gms., of methanol, was reacted with 297 gms., 1.0 moles of linseed acid chloride to produce the corresponding "fatty" ethenoid acylamino hydrochloride derivative with the average composition:

R$^4$ is a linseed acid chloride derivative

Example 8

Evaluation of "Fatty" Acylaminoorganosilanes as Multi-Functional Coupling Agents for Glass Fibers The procedure used to evaluate the performance of experimental silanes was as follows:

(1) Water sized glass fiber roving was treated with an aqueous solution of a candidate silane and dried in a slow speed laboratory treater.

(2) Silane loading (L.O.I.), abrasion resistance and stiffness of the silane sized roving was determined.

(3) Pulltruded rod composites were prepared using the experimental roving as reinforcement and employing a heat curing unsaturated polyester resin (Ashland Chem., Aropol 7240) as matrix. Flexural strength of the resulting composite was determined on dry specimens and for specimens that were immersed in boiling water (100° C.) for 24 hours.

The entire evaluation was repeated for selected silanes but they were evaluated as components of simulated total size (the other components were a film forming resin and a lubricant).

Performance parameters used to judge the performance of a silane were composite mechanical properties, both dry and wet, and roving abrasion resistance and stiffness.

A. Physical Properties of Sized Roving (1) Abrasion Resistance Test—A bundle of glass roving (about 2000 strands/bundle) sized with the appropriate formulation and 50 inches in length was tested for abrasion resistance by (a) being twisted into a "figure 8" position in order to provide a center contact point for self-abrasion and (b) rubbing at the center contact point at a rate of 116 cycles per minute using a tension of 192 grams. The time (minutes) to breaking of the bundle was measured.

Test used to measure the relative stiffness of various treatments on glass fibers consists of a flexural type test (see C below). This data was generated using a one inch span and a test speed of 0.2 inches per minute and is useful in comparing rovings of similar fiber diameter and number.

B. Preparation of Pulltruded Rods

Water-sized continuous strand glss roving (Owens Corning Fiberglas' "OCF861") was wrapped 22 times around a 38 inch steel frame and cut to form 22 lengths of roving about 6 feet long. These lengths of roving were tied together at one end using a piece of 20 gauge copper wire to form a bundle.

A resin mixture consisting of 1000 parts of Polyester A, 100 parts of styrene monomer and 10 parts of Catalyst I was prepared. The roving bundle was immersed in the resin formulation for several minutes prior to being drawn up a precision-bore glass tube having an inner diameter of 0.25 inches. The glass tube was pretreated with a silicon resin release agent. The drawing rate was about 3.5 inches per minute. The resulting pulltruded rods were placed in a forced air circulating oven at 100° C. and allowed to cure for 30 minutes.

C. Flexural strength tests were performed both on "dry" rods and "wet" rods which had been subjected to a 24 hour immersion in boiling water in accordance with ASTM-D349-261.

Example 9

Preparation of Linseed Acid Chloride From Linseed Acid and Thionyl Chloride (See Organic Synthesis, Vol. IV page 739).

Equipment Description and Experimental Procedures:

Into a one liter, three-necked flask, fitted with a dip-tube, inverted U-connecting tube and stopper, there is charged thionyl chloride.

Attached to the connecting tubes is a 2 foot column, packed with ⅛" glass helices, which is wrapped in electric heating tape. Atop the column is a T-connecting tube which holds a 500 ml addition funnel (The additional funnel may be taped for heating, as linseed acid may be a solid or viscous liquid depending on the supplier and purity) and is joined to a Friedrick condenser (By including the condenser, thionyl chloride is allowed to condense back to the starting kettle). By use of a Y-tube, the condenser and dip-tube are connected to a receiving flask. The open arm of the Y-tube is available for nitroen blow-by and to allow effluent gas escape. Below the 2 foot column is a "short leg" column, unpacked but taped for heating. (The heated "short leg" column, provides for a minimal amount of thionyl chloride to condense into the receiving flask.)

Linseed acid is delivered through the addition funnel while thionyl chloride is being distilled. Contact is made in the column at the reflux temperature of thionyl chloride. The product acid-chloride is collected in receiving flask and removed for thionyl chloride clean-up.

Performance Evaluation:

The procedure used to evaluate the performance of experimental silanes was as follows:

(1) Water sized glass fiber roving was treated with an aqueous solution of a candidate silane and dried in a slow speed laboratory treater.

(2) Silane loading (L.O.I.) abrasion resistance and stiffness of the silane sized roving was determined.

(3) Pulltruded rod composites were prepared using the experimental roving as reinforcement and employing a heat curing unsaturated polyester resin (Ashland Chem., Aropol 7240) as matrix. Flexural strength of the resulting composite was determined on dry specimens and for specimens that were immersed in boiling water (100° C.) for hours.

The silane utilized in this study are shown in Table I. This listing includes a number of controls (A, B and C), precursors for the experimental products and experimental silanes.

The thrust of the experimental samples was to determine if the inclusion of mono and/or bis-silyl functionality in an organofunction silane molecule would make a positive contribution to the materials performance when used as a coupling agent in fiber glass applications.

The by-product hydrogen chloride was either removed by the use of a tertiary amine hydrogen chloride acceptor or left in the product as an aminosilane salt. All of the experimental products were formulated as 50 wt % solutions in methanol.

TABLE II

Silane Compositions

| Example | |
|---|---|
| 1 | $CH_3(CH_2CH=CH)_3(CH_2)_7C(O)NHC_2H_4N(H)C_3H_6Si(OCH_3)_3 \cdot HCl$ |
| 2 | $CH_3(CH_2CH=CH)_3(CH_2)_7C(O)N(H)(C_2H_4H_4NH)_2C_3H_6Si(OCH_3)_3 \cdot HCl$ |
| 3 | Reaction Product 1 mole of $[(CH_3O)_3SiC_3H_6]_2NH$ and 1 mole of $CH_3(CH_2CH=CH)_3(CH_2)_7\overset{O}{\overset{\|}{C}}Cl$ |
| 4 | Reaction Product 1 mole of $[(CH_3O)_3SiC_3H_6]_2NH$ + 0.5 mole $CH_3(CH_2CH=CH)_3(CH_2)_7\overset{O}{\overset{\|}{C}}Cl$ formulated as a 50% MeOH solution. |
| 5 | Reaction Product 1 mole $[(CH_3O)_3SiC_3H_6NHCH_2]_2$ + 0.5 mole $CH_3(CH_2CH=CH)_3(CH_2)_7CCl$ formulated as a 50% MeOH solution. |

TABLE II-continued

| | Silane Compositions |
|---|---|
| Example | |
| A | $CH_2=C(CH_3)C(O)OC_3H_6Si(OCH_3)_3$ |

TABLE III

Composite and Fiber Properties of "Silane Only" Sized Glass Fibers

| | Composite Properties | | | Glass Fiber Properties | |
|---|---|---|---|---|---|
| | Flexural Strength PSI × 10⁻³ | | | Abrasion | Fiber |
| Silane | Dry | Wet | % Glass | L.O.I. Wt % | Resistance (Minutes) | Stiffness (Grams) |
| A | 95 | 80 | 62.5 | 0.23 | 0.8 | 12.6 |
| 1 | 97 | 64 | 61.9 | 0.16 | 5.4 | 4.4 |
| 2 | 92 | 76 | 62.3 | 0.34 | 6.7 | 10.8 |
| 3 | 97 | 85 | 62.2 | 0.27 | 7.0 | 12.4 |
| 4 | 92 | 88 | 61.8 | 0.28 | 5.3 | 10.4 |
| 5 | 88 | 72 | 61.6 | 0.33 | 4.7 | 25.4 |

TABLE IV

Composite and Fiberglass Properties Based on Silane Only Size

| Silane | Flexural Strength (psi) Dry | Wet[1] | Glass Content % | Size Loading | Abrasion Resistance[2] | Stiffness[3] |
|---|---|---|---|---|---|---|
| A | 113,000 | 90,000 | 65.9 | 0.25 | 1.4 | N/A |
| 1 | 107,000 | 63,000 | 65.4 | 0.33 | 15.1 | N/A |
| 2 | 101,000 | 74,000 | 65.1 | 0.44 | 20.4 | N/A |

[1]Immersed in boiling water for 24 hours.
[2]Time to failure in seconds in a glass on glass abrasion test.
[3]Too soft to measure.

TABLE V

Composite and Fiber Properties of "Silane Only" Sized Glass Fibers

| | Composite Properties | | | Glass Fiber Properties | |
|---|---|---|---|---|---|
| | Flexural Strength PSI × 10⁻³ | | | Abrasion | Fiber |
| Silane | Dry | Wet | % Glass | L.O.I. Wt % | Resistance (Minutes) | Stiffness (Grams) |
| A | 102 | 100 | 61.5 | 0.28 | 0.9 | 15.0 |
| 3 | 94 | 85 | 61.4 | 0.30 | 4.7 | 17.2 |
| 4 | 92 | 81 | 61.6 | 0.25 | 5.5 | 8.0 |
| 5 | 91 | 71 | 61.6 | 0.25 | 2.8 | 16.4 |

We claim:

1. A polyester resin composite reinforced with glass fibers said glass fibers having been treated with a coupling agent wherein the coupling agent comprises a fatty ethenoid acylaminoorganosilicon compound represented by the general formula $$Y[N(Y)_cR_{2-c}]_x[N(W)R^1]_y[N(Y)_bR^2_{2-b}]_z(HX)_w$$

wherein R and $R^1$ are individually selected from the group consisting of divalent alkylene groups containing from two to six carbon atoms inclusive, divalent arylene groups containing from six to twelve carbon atoms inclusive, divalent alkyl substituted arylene groups containing from seven to twenty carbon atoms inclusive, and a divalent group of the formula

wherein $R^3$ is a divalent alkylene group containing from two to six carbon atoms inclusive; $R^2$ is a monovalent alkyl or aryl group containing from one to ten carbon atoms or hydrogen; W is either hydrogen or

wherein $R^4$ is a monovalent hydrocarbon group containing from 8 to 24 carbon atoms and containing at least one double bond; Y is selected from the group consisting of hydrogen;

wherein $R^4$ is as defined above; $R^2$; and $-R^5Si(OR^6)_{3-a}(R^7)_a$ wherein $R^5$ is a divalent alkylene group containing from two to six carbon atoms inclusive, $R^6$ and $R^7$ are individually a monovalent alkyl or aryl group containing from one to six carbon atoms inclusive; and $R^6$ may also be a silicon containing moiety wherein the oxygen atom is directed bonded to the silicon atom of the $R^6$ silicon containing moiety; and a has a value of zero, one or two; b has a value of zero, one or two; c has a value of zero or one; x and y have values such that x+y equal one to thirty with the proviso that x is at least one; z is zero or one; X is a halogen atom or an ester, hydroxyl or anhydride group; w has a value equal to from zero to the sum of x+y+z provided that w does not exceed the total nitrogen atom in free amine form; with the proviso that at least one Y is $-R^5Si(OR^6)_{3-a}(R^7)_a$; and at least one other Y is

and when x=1, y=0 and z=0 then c=1.

* * * * *